United States Patent

Strauss et al.

[11] Patent Number: 5,871,473
[45] Date of Patent: Feb. 16, 1999

[54] CANNULA HOUSING CONNECTION

[75] Inventors: Douglas W. Strauss, Hamden; William J. Vumback, Northford, both of Conn.

[73] Assignee: United States Surgical Corporation, Norwalk, Conn.

[21] Appl. No.: 726,104

[22] Filed: Oct. 4, 1996

[51] Int. Cl.$^6$ ........................................................ A61M 5/00
[52] U.S. Cl. ............................................ 604/256; 128/912
[58] Field of Search ..................................... 604/164, 167, 604/169, 246, 247, 256, 264, 272, 280, 283, 905; 128/912, DIG. 26

[56] References Cited

U.S. PATENT DOCUMENTS

| | | |
|---|---|---|
| 1,531,213 | 3/1925 | Nimmer . |
| 4,535,773 | 8/1985 | Yoon . |
| 4,609,370 | 9/1986 | Morrison . |
| 4,649,904 | 3/1987 | Krauter et al. . |
| 4,655,752 | 4/1987 | Honkanen et al. . |
| 4,769,018 | 9/1988 | Wilson . |
| 4,943,280 | 7/1990 | Lander . |
| 5,104,383 | 4/1992 | Shichman . |
| 5,112,321 | 5/1992 | Hiltebrandt . |
| 5,211,633 | 5/1993 | Stouder, Jr. . |
| 5,226,426 | 7/1993 | Yoon . |
| 5,242,412 | 9/1993 | Blake, III . |
| 5,261,888 | 11/1993 | Semm . |
| 5,300,035 | 4/1994 | Clement . |
| 5,307,702 | 5/1994 | Spellman et al. . |
| 5,324,270 | 6/1994 | Kayan et al. . |
| 5,356,158 | 10/1994 | Simmons et al. . |
| 5,380,302 | 1/1995 | Orth .......................................... 604/164 |
| 5,383,860 | 1/1995 | Lau . |
| 5,411,367 | 5/1995 | Walker . |
| 5,423,579 | 6/1995 | Blose et al. . |
| 5,431,415 | 7/1995 | Millonig et al. . |
| 5,456,673 | 10/1995 | Ziegler et al. . |
| 5,472,216 | 12/1995 | Albertson et al. . |
| 5,484,284 | 1/1996 | Bailey . |
| 5,507,498 | 4/1996 | Trott . |
| 5,534,009 | 7/1996 | Lander .................................... 604/164 |
| 5,549,583 | 8/1996 | Sanford et al. ........................ 604/905 |

FOREIGN PATENT DOCUMENTS

WO 93/04717  3/1993  WIPO .

*Primary Examiner*—Wynn Wood Coggins
*Assistant Examiner*—Sharon Finkel

[57] ABSTRACT

A surgical cannula assembly includes a cannula, an adapter ring, and a housing. The adapter ring is defined at the proximal end portion of the cannula and includes a first sealing surface. The housing includes a port structure for engagement with the adapter ring. The port has a lip with a second sealing surface adapted to engage the first sealing surface. The first and second sealing surfaces are preferably annular surfaces which are non-parallel with respect to each other.

16 Claims, 5 Drawing Sheets

5,871,473

CANNULA HOUSING CONNECTION

BACKGROUND

1. Technical Field

The disclosure herein relates to a cannula assembly for use in surgical procedures, and particularly to a cannula housing connection.

2. Background of Related Art

Cannula assemblies are typically used in minimally invasive surgical procedures such as laparoscopic, endoscopic, and arthroscopic operations. In minimally invasive procedures the operating instrumentation is typically deployed through a narrow cannula inserted through a small opening or incision in the body to reach an interior operating site. In some procedures, for example abdominal surgery, the body cavity is insufflated with an inert gas. Cannula assemblies are often required to have a seal to prevent the egress or entry of fluids from or into the body. For example, some cannula assemblies include a flapper valve to provide a seal between the cannula assembly and the instrumentation deployed therethrough. See for example, U.S. Pat. No. 4,943,280 to Lander, herein incorporated by reference, which discloses a self sealing flapper valve for an insufflation cannula assembly.

Also, sealing is generally required between the cannula itself and the housing to which it is connected. For example, an O-ring or other gasket, is often used as a sealing component between the cannula tube and the housing, either alone or incombination with glues, adhesives, sonic welding, or the like.

It would be advantageous in certain situations, however, to have a connectable cannula and housing which facilitate sealing and which might be effectuated by the user of the product.

SUMMARY

A cannula assembly is provided which includes: (i) a cannula defining a longitudinal axis and having a free distal end and a proximal end portion; (ii) an adapter ring defined at the proximal end portion of the cannula, the adapter ring having a first sealing surface oriented at a first angle relative to the longitudinal axis; and (iii) a cannula housing having a port structure for association with the adapter ring. The port structure includes a second sealing surface for sealing contact with the first sealing surface, the second sealing surface being oriented at a second angle from the longitudinal axis, the second angle differing from the first angle by from about 3° to about 10°.

Manual engagement of the adapter ring and housing, e.g., through threading or the like, enables disassembly and replacement of the cannula assembly components by the user of the product. Advantageously, interaction between the first and second sealing surfaces obviates the need for a separate sealing member, such as a gasket or O-ring, to obtain a fluid tight seal.

BRIEF DESCRIPTION OF THE DRAWINGS

Various embodiments are described below with reference to the drawings wherein.

DETAILED DESCRIPTION OF PREFERRED EMBODIMENTS

In the description which follows, the term "proximal", as is traditional, will refer to the portion of the structure which is closest to the operator, while the term "distal" will refer to the portion which is furthest from the operator.

Figure 1:
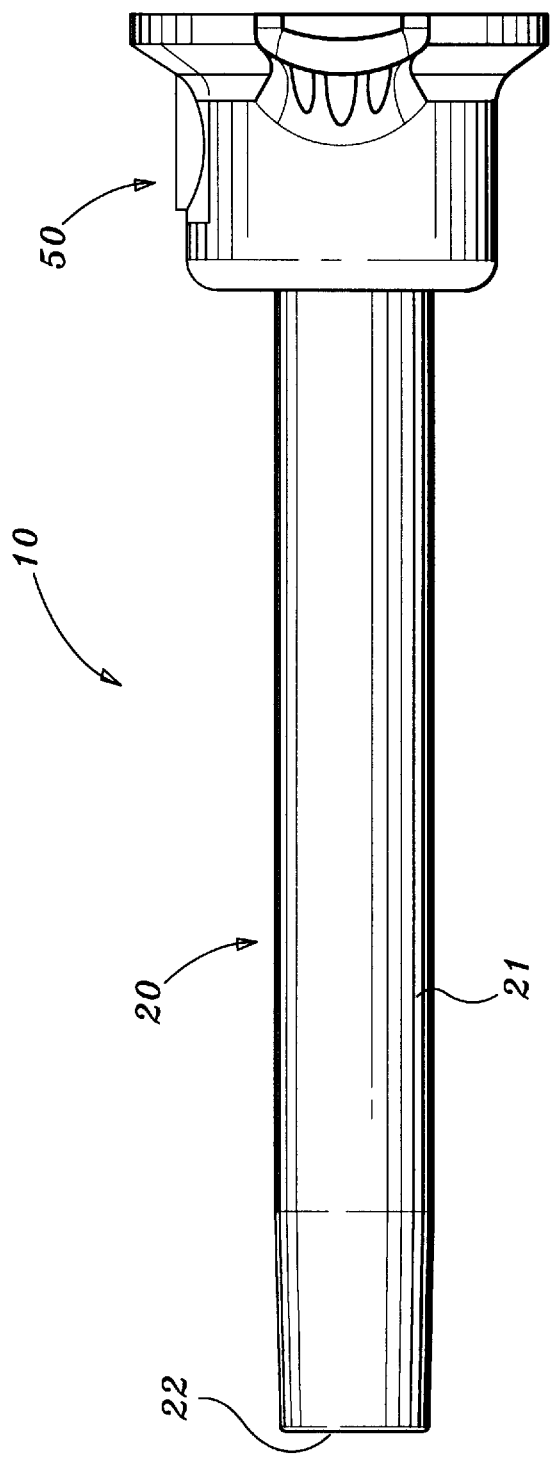
FIG. 1 is a side elevational view showing a cannula assembly according to the present disclosure.
Figure 2:
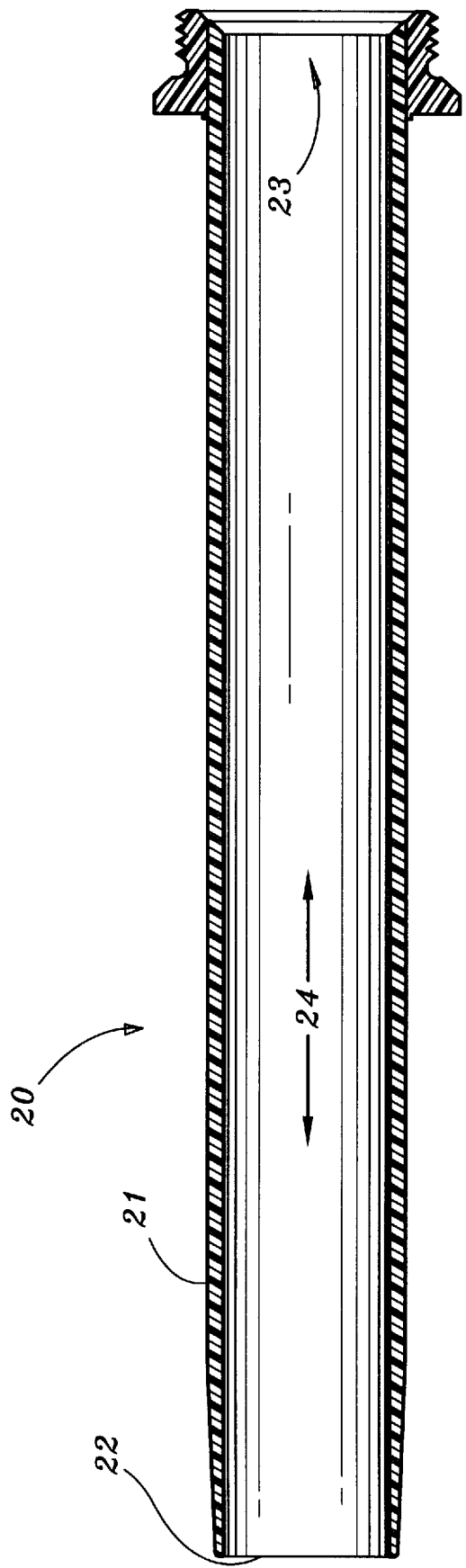
FIG. 2 is a sectional side view of a cannula which defines an adapter ring at the proximal end thereof.

Referring now to FIGS. 1 and 2, the cannula assembly 10 includes a cannula 20, which is designed for connection to a cannula housing 50. Cannula 20 is a tubular body 21 having a distal end 22, a proximal end portion 23 and an axial bore 24, and defines a longitudinal axis of the cannula assembly 10. Cannula 20 is distally insertable into an incision or other small opening in a wall of body tissue to gain access to an operating site and is typically from about 70 mm to about 150 mm in length and defines an aperture of from about 3 mm to about 15 mm in diameter. The housing 50 can optionally contain a flapper valve or other sealing mechanism (not shown) for gaseous sealing both in the absence and in the presence of a surgical instrument and optionally a stopcock port (not shown) for introduction of inert gas for insufflation. See, for example, U.S. Pat. No. 4,943,280.

Figure 3:
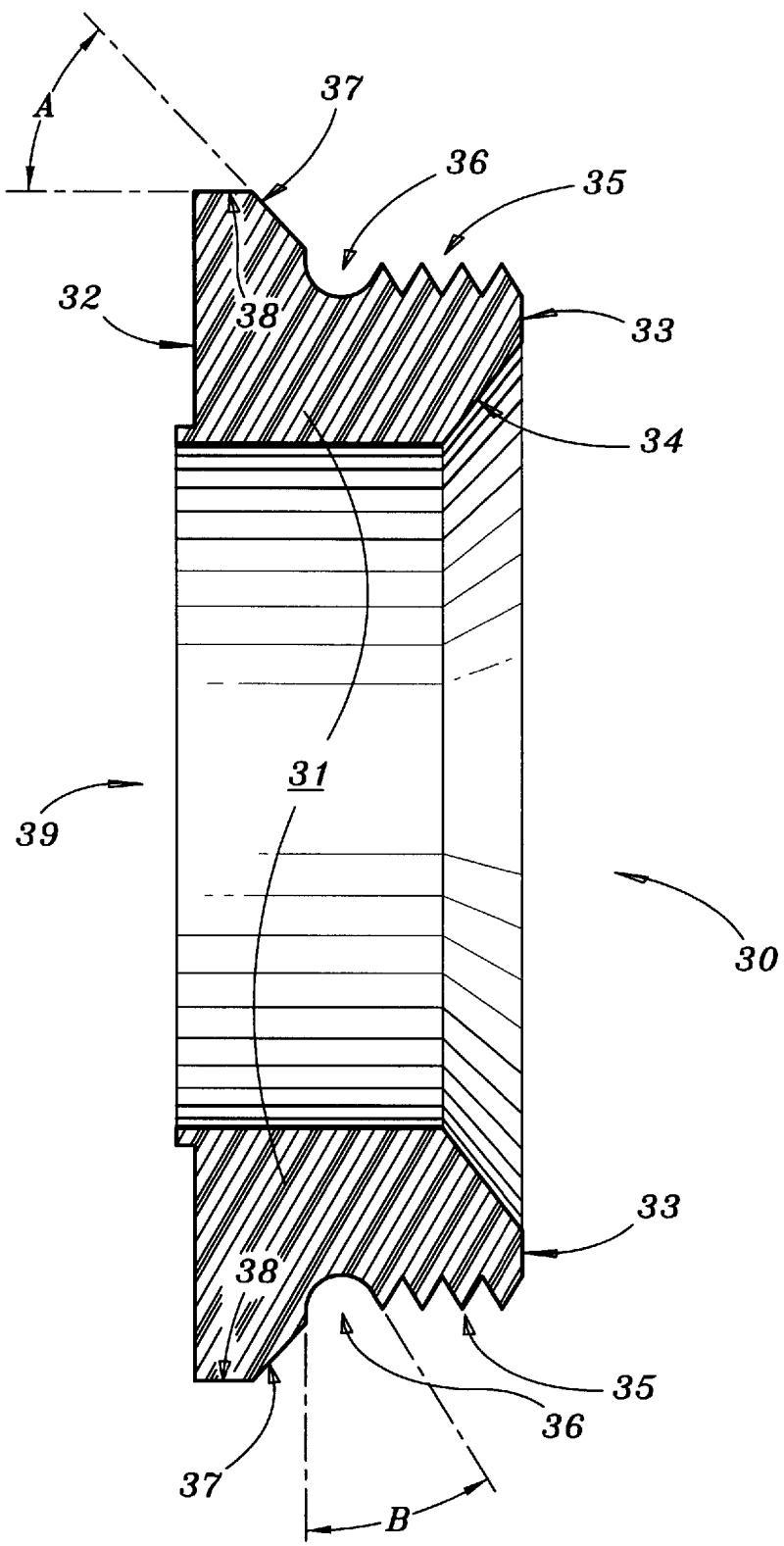
FIG. 3 is a sectional side view of the adapter ring.

Referring now to FIGS. 2 and 3, an adapter ring 30 serves as an adapter to connect the cannula 20 to the housing 50. Adapter ring 30 may be formed on or fixedly mounted (e.g., by welding, gluing or mechanical interaction) to the proximal end portion 23 of cannula 20. Adapter ring 30 generally includes a cylindrical body 31 having an annular distal end surface 32, an annular proximal end surface 33, a bevelled interior annular surface 34, a threaded exterior circumferential surface 35, a circumferential notch 36, a proximally facing angled annular sealing surface 37, a circumferential outer surface 38 and an interior bore 39. In designs wherein adapter ring 30 is a distinct member from cannula 20, interior bore 39 provides a passage through which the proximal end portion 23 of cannula 20 may be disposed.

Circumferential notch 36 typically takes the form of an undercut which helps to ensure that the interconnection of cannula 20 with cannula housing 50, e.g., through interacting threads, does not bottom-out before annular sealing surface 37 effectively seals with a corresponding sealing surface on housing 50, as discussed hereinbelow. Sealing surface 37 is generally oriented at an angle A of from about 40° to about 50° with respect to the longitudinal axis of cannula assembly 10 and, preferably, angle A ranges from about 44° to about 46° relative to the longitudinal axis. Sealing surface 37 is adapted to engage a corresponding sealing surface 57 in housing 50, as explained below. Threaded surface 35 is adapted to engage a corresponding threaded surface 55 on housing 50.

Adapter ring 30 is preferably fabricated from a metal alloy, e.g., titanium, or other suitable biocompatible material having strength and resilience sufficient for the purposes described herein. In designs where adapter ring 30 and cannula 20 are fabricated as an integral member, such integral member is preferably fabricated from a suitable metal or biocompatible plastic, preferably a material that may be cleaned, sterilized and used on multiple occasions.

Figure 4:
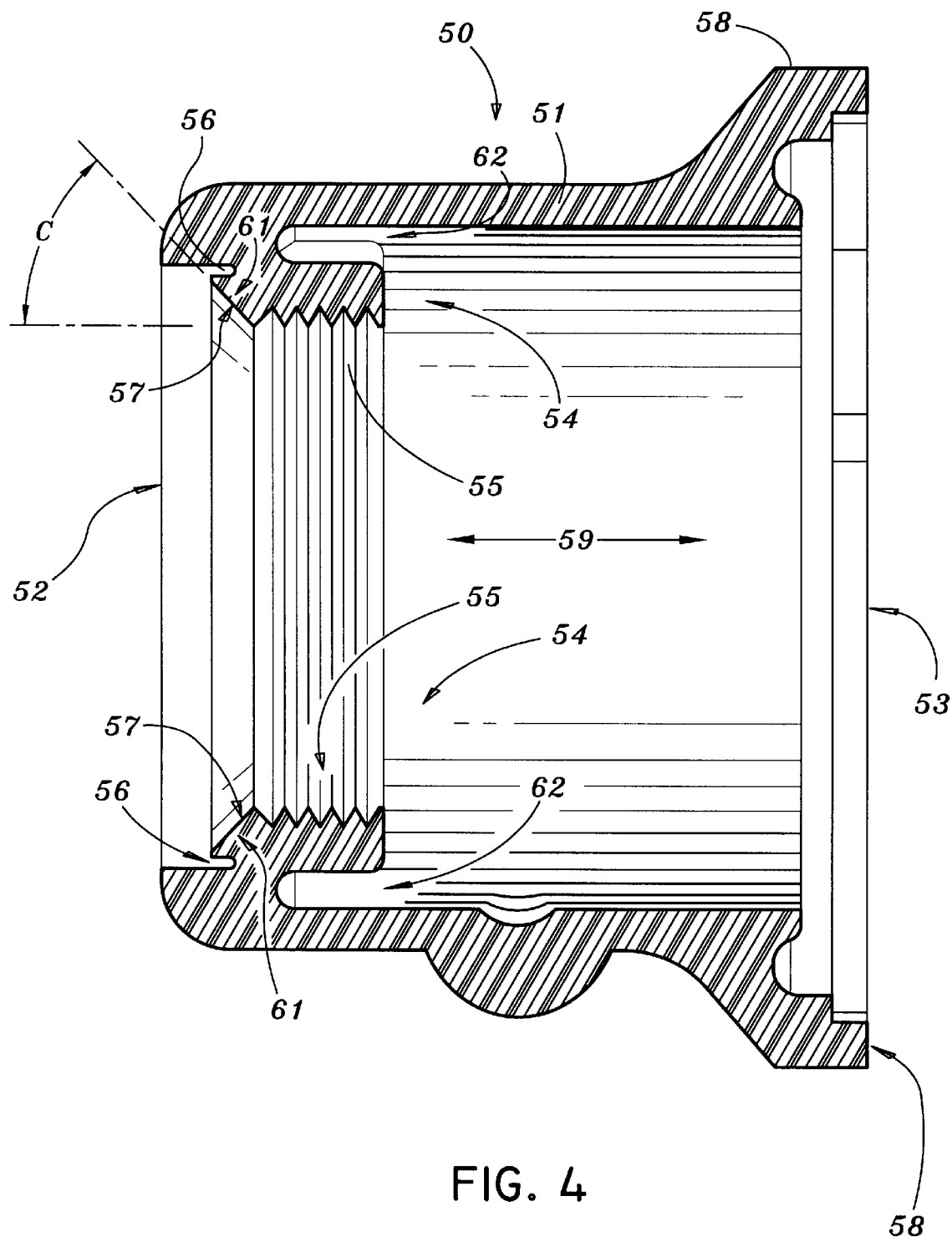
FIG. 4 is a sectional side view of a cannula housing.
Figure 5:
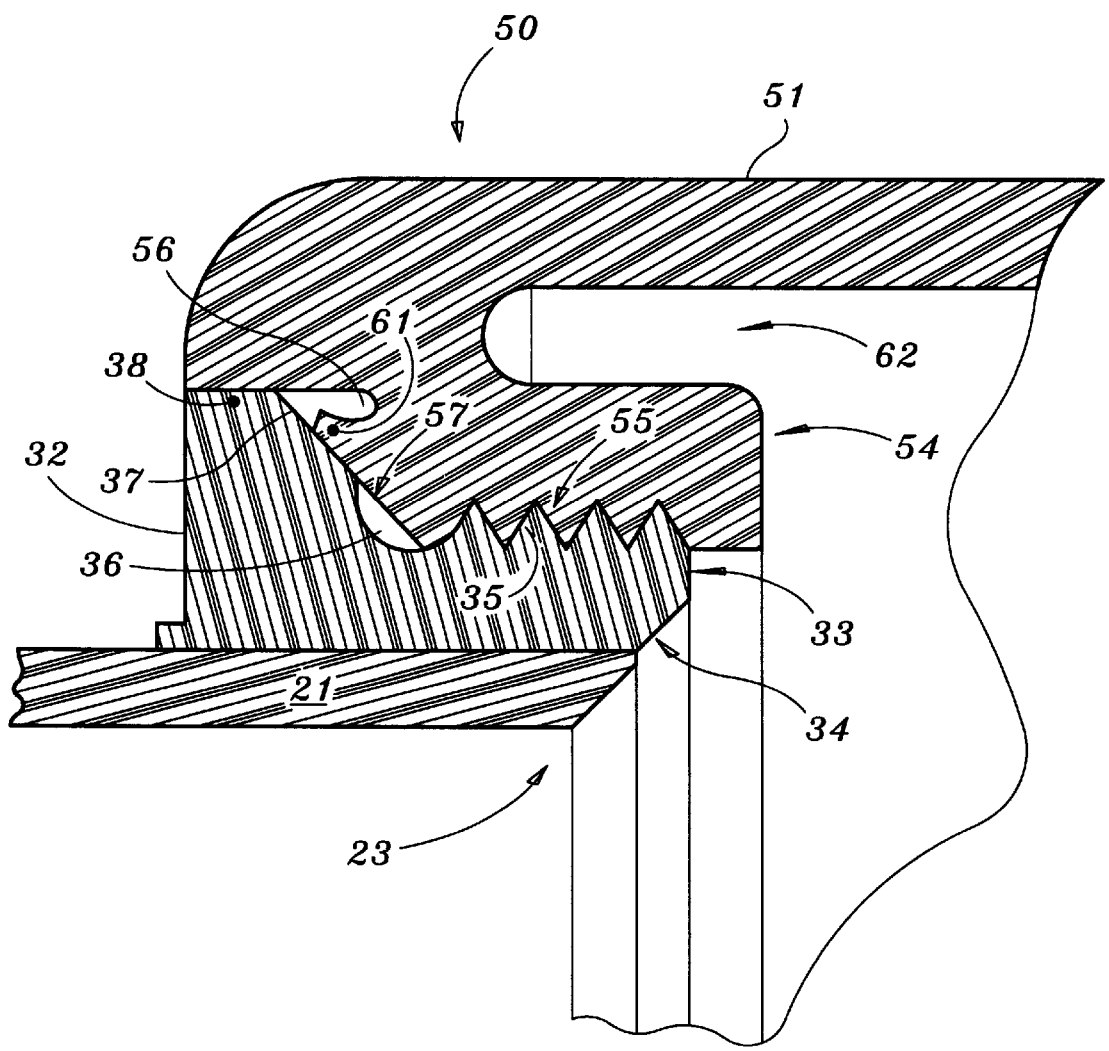
FIG. 5 is a detailed sectional view of the joint between the adapter ring and the cannula housing.

Referring now to FIGS. 4 and 5, housing 50 is also fabricated from a suitable biocompatible material, e.g., a plastic material such as ABS, and typically includes a generally cylindrical wall 51 connected to a proximal flange portion 58, a distal end 52, a proximal end 53, and an axial bore 59 extending therethrough. An important feature of cannula assembly 10 is the port structure 54 in cannula housing 50, which is adapted to interact with and sealingly engage adapter ring 30.

Port structure 54 defines an opening adapted to receive adapter ring 30 and includes a threaded surface 55 adapted to engage threaded surface 35 of adapter ring 30. Port structure 54 also includes an annular lip 61 having a distally facing angled annular sealing surface 57 which is adapted to contact corresponding sealing surface 37, a circumferential notch 56 in the vicinity of sealing surface 57, and a circumferential notch 62 providing a space between port structure 54 and wall 51. Notch 56 advantageously allows flexure when sealing surface 57 engages sealing surface 37 of adapter ring 30, thereby facilitating sealing engagement therebetween.

Sealing surface 57 is oriented at an angle C of preferably from about 30° to about 43° with respect to the longitudinal axis of cannula 20 and more preferably, angle C ranges from about 39° to about 41° with respect to the longitudinal axis. Sealing surfaces 57 and 37 define annular planes which, prior to contact therebetween, are in substantially non-parallel relationship to each other. The difference between angle C and angle A preferably ranges from about 3° to about 10° and more preferably from about 4° to about 6°. Angle C is preferably less than angle A although, in the alternative, angle C can be greater than angle A by a differential in the range set forth above.

As noted above, circumferential notch 56 is sized to permit resilient outward flexing of lip 61 sufficient to insure that the contact between sealing surfaces 37 and 57 provides a fluid tight seal. Circumferential notch 62 advantageously permits resilient flexing of the port 54 sufficient to provide for a secure engagement between threaded surfaces 55 and 35.

The threaded engagement between the housing 50 and the insert 30 enables the cannula assembly to be disassembled for the substitution or replacement of one or more components (e.g. cannula 20 and/or housing 50) while providing for a fluid tight seal with a corresponding substituted component. Such disassembly may also facilitate separate cleaning and/or sterilization of respective components, and may permit pairing of housings and/or cannulas of various sizes. Thus, a housing 50 adapted to accommodate instruments of one diameter, e.g., up to 10 mm, may be affixed to a cannula 20 designed to accommodate instruments of a different diameter, e.g., 5 mm and less, thereby increasing the flexibility and potential cost effectiveness of the cannula assembly. It is also contemplated that the assembly/disassembly system described herein may prove advantageous in the mass production of cannula assemblies that are not intended to be disassembled and reassembled by product users.

It will be understood that various modifications may be made to the embodiments disclosed herein. For example, various materials of construction may be used. The housing 50 may contain other sealing means such as flapper valves, iris valves, duck valves, and the like. Therefore, the above description should not be construed as limiting, but merely as exemplifications of preferred embodiments. Those skilled in the art will envision other modifications within the scope and spirit of the claims appended hereto.

What is claimed is:

1. A surgical cannula assembly which comprises:
   a) a cannula defining a longitudinal axis and having a free distal end and a proximal end portion;
   b) an adapter ring defined at the proximal end portion of the cannula, the adapter ring having a first sealing surface oriented at a first angle relative to the longitudinal axis; and
   c) a housing having a port structure for sealing engagement with the adapter ring, the port structure including a second sealing surface for sealing contact with the first sealing surface, the second sealing surface being oriented at a second angle from the longitudinal axis, the second angle differing from the first angle by from about 3° to about 10°.

2. The cannula assembly of claim 1, wherein the first sealing surface is an annular surface.

3. The cannula assembly of claim 1 wherein the first angle ranges from about 40° to about 50°.

4. The cannula assembly of claim 1 wherein the second angle ranges from about 30° to about 40°.

5. The cannula assembly of claim 1 wherein the second angle differs from the first angle by from about 4° to about 6°.

6. The cannula assembly of claim 1 wherein the second angle is less than the first angle.

7. The cannula assembly of claim 1 wherein the second angle is more than the first angle.

8. The cannula assembly of claim 1, wherein the second sealing surface is an annular surface.

9. The cannula assembly of claim 1 wherein the adapter ring includes a threaded surface for engagement with a corresponding threaded surface of the housing.

10. The cannula assembly of claim 1 wherein the port structure further includes a resiliently flexible annular lip.

11. In combination with a surgical cannula having a longitudinal axis, a housing which includes:
   a port structure for reception therein of the surgical cannula, the surgical cannula having a first sealing surface oriented at a first angle with respect to the longitudinal axis, the port structure including a lip with an annular second sealing surface for sealing contact with the first sealing surface, the second sealing surface being in non-parallel relationship to the first sealing surface prior to contact therebetween.

12. In combination with a housing, a replaceable cannula structure for connection with the housing to form a surgical cannula assembly, the cannula structure comprising:
   a) a tubular member defining a longitudinal axis and having a free distal end and a proximal end portion;
   b) an adapter ring connected to the proximal end portion of the cannula, the adapter ring having a first sealing surface oriented at a first angle from the longitudinal axis; the adapter ring being configured for engagement with the housing, the housing having a port structure including a lip with an annular second sealing surface for sealing contact with the first sealing surface, the second sealing surface being in non-parallel relationship to the first sealing surface prior to contact therebetween.

13. The replaceable cannula structure of claim 12 wherein the second angle differs from the first angle by from about 3° to about 10°.

14. A surgical cannula assembly which comprises:
   a) a replaceable cannula structure which includes
      a tubular member defining a longitudinal axis and having a free distal end and a proximal end portion, and
      an adapter ring defined at the proximal end portion of the cannula, the adapter ring having a first threaded surface and a proximally facing first annular sealing surface oriented at a first angle relative to the horizontal axis; and
   b) a housing which includes a distal port structure for removable reception therein of the adapter ring, the port structure including an interior lip with a second threaded surface engageable with the first threaded surface and a distally facing second annular sealing surface for sealing contact with the first annular sealing surface, the second annular sealing surface being in non-parallel relationship to the first sealing surface prior to contact therebetween.

16. The surgical cannula assembly of claim 14 wherein the first threaded surface is proximal to the first annular sealing surface and the second threaded surface is proximal to the second annular sealing surface.

15. The surgical cannula assembly of claim 14 wherein the first annular sealing surface and the second annular sealing surface are oriented at respective angles which differ from each other by from about 3° to about 10°.

* * * * *